United States Patent [19]
Dervieux

[11] Patent Number: 4,920,981

[45] Date of Patent: May 1, 1990

[54] APPARATUS FOR RELIEF OF PAIN AND CONTRACTIONS USING DISCHARGES OF SPARKS ADJUSTABLE IN INTENSITY OF PIEZO-ELECTRIC ORIGIN WITH A BIPOLAR ELECTRODE OF WHICH ONE OF THE POLES IS IN DIRECT CONTACT WITH THE SKIN AND THE OTHER SPACED THEREFROM

[75] Inventor: Dominique Dervieux, Nice, France

[73] Assignee: Societe Anatomia - La Boutique du Dos, Paris, France

[21] Appl. No.: 97,964

[22] PCT Filed: Dec. 24, 1986

[86] PCT No.: PCT/FR86/00449

§ 371 Date: Sep. 30, 1987

§ 102(e) Date: Sep. 30, 1987

[87] PCT Pub. No.: WO87/04068

PCT Pub. Date: Jul. 16, 1987

[30] Foreign Application Priority Data

Dec. 31, 1985 [FR] France ................................ 85 19590

[51] Int. Cl.[5] ................................................ A61N 1/32

[52] U.S. Cl. .................................................... 128/800

[58] Field of Search ............... 128/783, 800, 801, 741, 128/907, 303.13, 303.14, 303.17, 419 R, 303.18; 361/232

[56] References Cited

U.S. PATENT DOCUMENTS 3,994,300 11/1976 Siddons .......................... 128/303.18
4,043,342 8/1977 Morrison, Jr. .
4,476,862 10/1984 Pao .
4,572,194 2/1986 Head ............................... 128/419 R
4,741,347 5/1988 Robert et al. ....................... 128/800

FOREIGN PATENT DOCUMENTS 2500745 9/1982 France .
2563735 11/1985 France .

*Primary Examiner*—Lee S. Cohen
*Attorney, Agent, or Firm*—Young & Thompson

[57] ABSTRACT

An apparatus using discharges of sparks especially of piezo-electric origin comprises a bipolar electrode which includes one or several metallic electrodes (5) for direct contact with the skin, connected to one pole as well as one or several discharge electrodes (6) connected to the other pole, isolated by way of an isolating separation, or by distance and permitting discharge of sparks against the skin by automatically spacing the metallic discharge electrode (6).

12 Claims, 4 Drawing Sheets

FIG.12
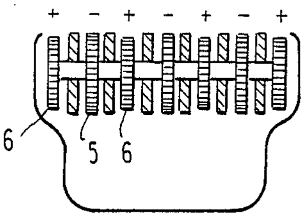
FIG.13
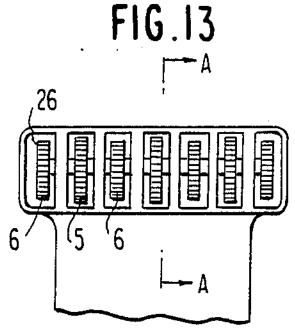
FIG.14
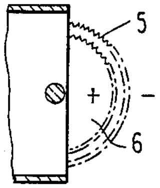
FIG.15
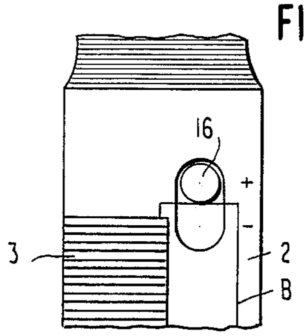
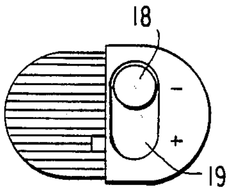
FIG.17
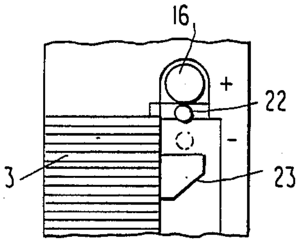
FIG.16
FIG.19
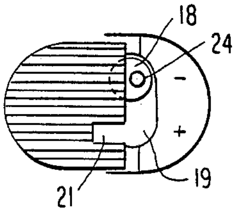

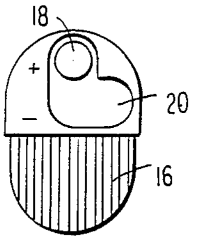
FIG.18
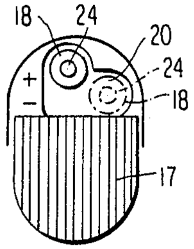
FIG.20
FIG.21
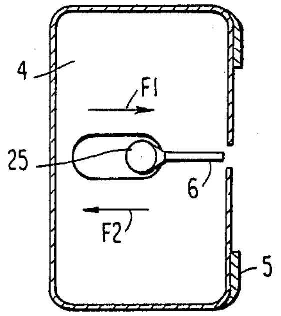
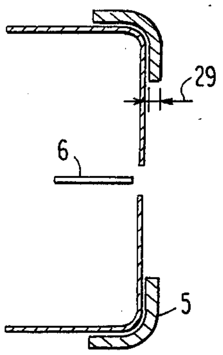
FIG.23
FIG.22
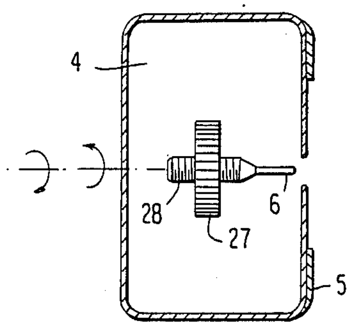
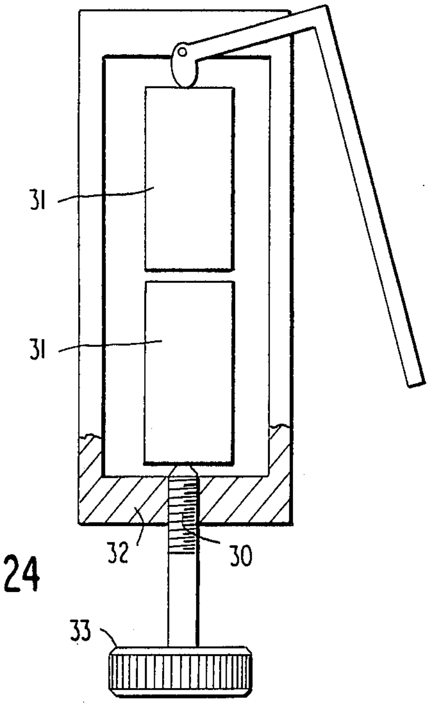
FIG.24

APPARATUS FOR RELIEF OF PAIN AND CONTRACTIONS USING DISCHARGES OF SPARKS ADJUSTABLE IN INTENSITY OF PIEZO-ELECTRIC ORIGIN WITH A BIPOLAR ELECTRODE OF WHICH ONE OF THE POLES IS IN DIRECT CONTACT WITH THE SKIN AND THE OTHER SPACED THEREFROM

BACKGROUND OF THE INVENTION

The invention has as an object an apparatus for relief of pain and contractions using discharges of sparks especially of piezo-electric origin, of which one of the poles is in direct contact with the skin.

BRIEF DESCRIPTION OF THE PRIOR ART

The state of the art can be defined by the following patents: FR-A-1,092,420, FR Addition 65,169, DE 2,117,917 and the DERVIEUX patents No. 2,500,745 and 2,563,735.

DERVIEUX patent No. 2,500,745 describes an apparatus with a unipolar electrode, one electrode of which is grounded either by a plate held by the patient, or by an already implanted electrode, or the patient is in contact with a handle which is conductive (which has several disadvantages).

DERIVEUX patent No. 2,563,735 describes an apparatus using bipolar electrodes discharging sparks of which the individual characteristics, shape, and the characteristics of their support permit the apparatus to be at a certain distance from the skin by means of an isolating separation.

This apparatus also has several disadvantages.

Thus, this apparatus does not permit discharging the same sparks on moist skin, or adjustment of the intensity.

The apparatus according to the invention seeks to improve this latter apparatus.

SUMMARY OF THE INVENTION

To this end, the apparatus comprises a bipolar electrode which comprises one or several metallic electrodes for direct contact with the skin connected to a pole, as well as one or several discharge electrodes for the other pole, isolated from the first and permitting discharge of sparks against the skin by automatically spacing the metallic discharge electrode.

The apparatus may comprise a means permitting varying the intensity of the spark discharges and/or varying the spacing of the discharge electrodes with respect to the skin:

(1) the apparatus may comprise a means serving as an adjustable abutment which permits varying the course of the articulated handle which actuates the piezo-electric generator of the mechanical type, and thus permits decreasing the intensity and adapting the emitted current to the sensitivity of the subject being treated.

(2) the apparatus may comprise a means automatically and adjustably spacing the spark-discharging electrode from the skin, or from the plane of contact serving as the contact electrode, either by a means acting as a roller or by a pushbutton provided, if desired, with a gear reduction lever having two or more positions.

BRIEF DESCRIPTION OF THE FIGURES

The accompanying drawings given by way of indicative and non-limiting example will permit easy understanding of the invention. They show a preferred embodiment according to the invention.

FIGS. 4 to 14 are views of various heads of the apparatus showing the characteristics especially of the contact electrode.

FIGS. 4 and 5 are front and side views of a central contact electrode.

FIGS. 6 and 7 are front and side views of a peripheral contact electrode.

FIGS. 8 and 9 are front and side views of a contact electrode having small cavities.

FIGS. 10 and 11 show an embodiment wherein the contact electrode is a peripheral electrodes as in the embodiment shown in FIGS. 6 and 7, but where there are two spark-discharging electrodes 6.

FIGS. 12 and 13 show an embodiment wherein the electrodes are formed as toothed wheels of different diameter and polarity (body contacting the skin-rollers spaced therefrom).

FIG. 14 is a side view along the line A—A shown in FIG. 13.

FIGS. 15 and 16 show a detail of the apparatus at the level of the button for varying the intensity.

FIGS. 17 and 19 show an embodiment wherein the adjusting button is disposed at the level of the end of the sleeve (and/or of the handle) and wherein the slot is longitudinal.

FIGS. 18 and 20 show an embodiment wherein the adjusting button is disposed at the end of the sleeve (and/or of the handle) and wherein the slot comprises a leg.

FIGS. 21, 22 and 23 are sectional views of the apparatus showing the means permitting adjusting the spacing of the spark-discharging electrode from the skin or from the plane serving as the contact electrode. One may be displaced with respect to the other.

DETAILED DESCRIPTION

Figure 3:
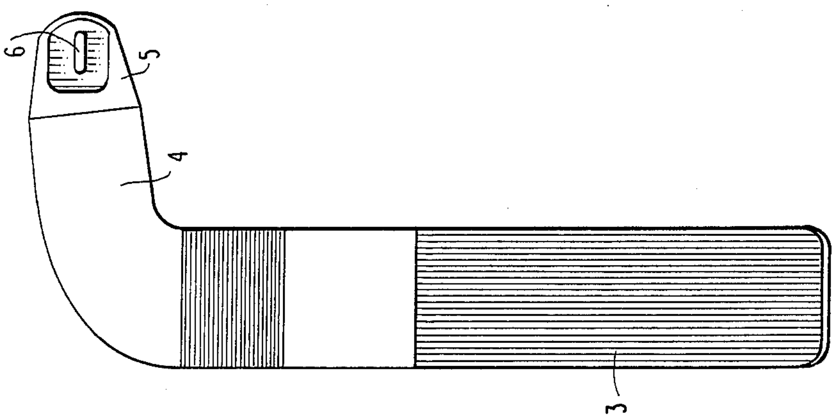
FIG. 3 is a side view of the apparatus.

The apparatus according to the invention is composed of a principal body 1 which forms a sleeve 2 comprising an articulated handle 3 and a fixed or removable head 4 that carries the bipolar electrodes 5 and 6.

The articulated handle 3 actuates, in a known mechanical manner, a piezo-electric generator.

Figure 1:
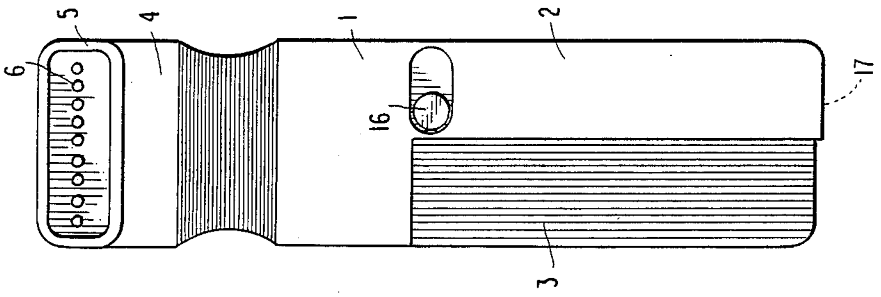
FIG. 1 is a front view of the apparatus.

According to FIG. 1, the apparatus comprises a bipolar electrode which comprises a metallic electrode 5 for direct contact with the skin. This contact electrode 5 forms in this example the head 4 of the apparatus, it assures direct contact with the skin, and it is connected to one pole.

One or several spark-discharging electrodes 6 of the other pole are disposed in the median and transverse portion of the head 4.

The electrode 5 for direct contact with the skin automatically maintains the spark-discharging electrode 6 spaced from the skin (from several dozen to several millimeters from the skin). To this end, the points of the discharge electrode 6 are shorter than the height of the border of the contact electrode 5 (ground). Sparks may thus be produced from the discharge electrodes 6 to the contact electrode 5.

A luminous indicator 7 permits verifying correct operation of the apparatus when the articulated handle 3 which actuates the piezo-electric generator is pressed and released.

Figure 4:
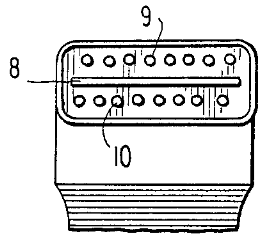
Figure 5:
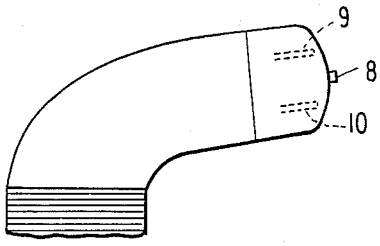

In FIGS. 4 and 5, a contact electrode 8 is centrally disposed. It forms a contact strip 8 which is disposed in the median portion and transversely of the head 4 of the apparatus. On either side of the contact strip 8 are disposed the other bipolar electrodes for discharging sparks against the skin, which form a range 9 and 10 on each side of the contact strip 8.

It will be understood, according to another embodiment not shown in the drawings, that there may be one or several contact electrodes or electrodes for discharging sparks against the skin.

Figure 2:
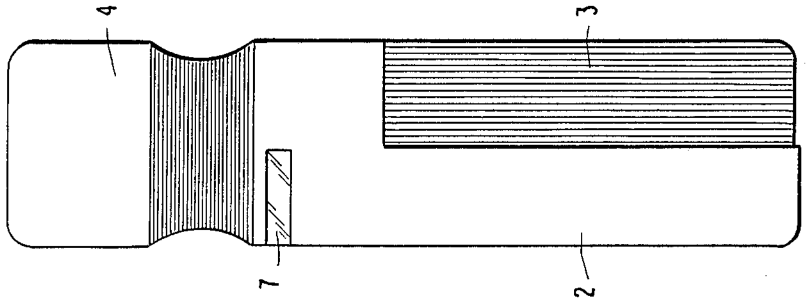
FIG. 2 is a rear view of the apparatus.
Figure 6:
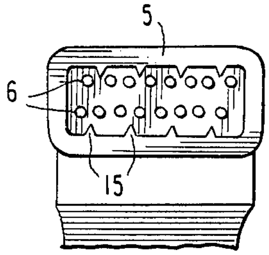
Figure 7:
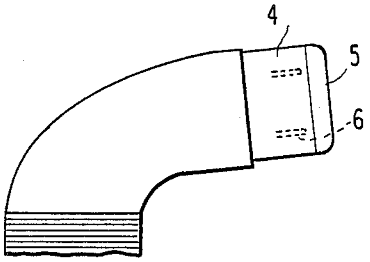

FIGS. 6 and 7 are detailed views of the electrodes already described above (see FIGS. 1, 2 and 3) and which show a peripheral contact electrode 5 and two discharge electrodes 6.

The points 15 formed by the peripheral contact electrode 5 promote discharge of sparks between one or several discharge electrodes, here the two ranges 5 and 6 toward which these points are directed, they discharge sparks at the time of operation without directly contacting the skin (through the air: between the electrodes or through a tissue on the skin).

Figure 8:
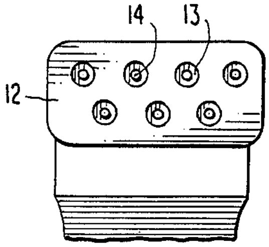
Figure 9:
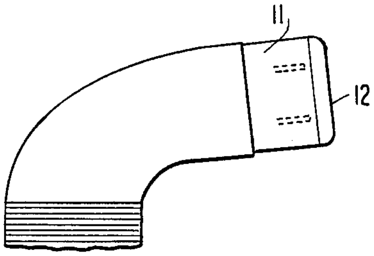

FIGS. 8 and 9 are detailed views of an electrode 11 which forms a contact plate 12 provided with one or several small cavities 13 the central portion of each of which is occupied by the point of a spark-discharging electrode 14.

The point of the electrode 14 is recessed relative to the plane of the contact plate 12 of the electrode 11.

Figure 10:
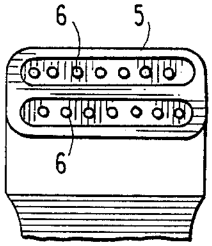
Figure 11:
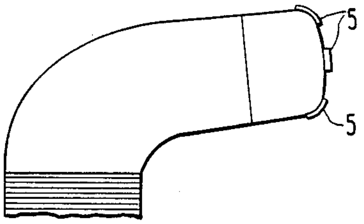

FIGS. 10 and 11 are detailed views of an electrode which forms a contact plate 5 provided with two cavities of which the central portion is occupied by a range of spark-discharging points 6.

The apparatus shown in FIGS. 12, 13 and 14 has a head composed of rollers 26, here toothed and movable, having different diameter and polarity:

- grounding in contact with the skin via contact roller electrode 5 (see FIG. 12);
- electrode 6 for discharging sparks against the skin composed of toothed and movable rollers 26 having a diameter slightly less than the diameter of the contact rollers 5.

Moreover, according to another embodiment not shown, there could be electrodes having solely parallel circular arcs, fixed or not, and toothed or smooth.

According to FIGS. 15 and 16 a button 16 permits adjusting the intensity of the spark discharge by varying the path of the articulated handle 3. The longer the path of the articulated handle 3, the greater the intensity. FIG. 15 shows a detail of the apparatus at the level of the button 16 for adjusting the intensity. FIG. 16 is a view according to FIG. 15 in which a window B has been opened to show the mechanism of the button 16. Specifically, the button 16 displaces an abutment 22 which limits the course of the articulated handle 3 at the level of its own abutment 23. The course of this button may be horizontal.

According to FIGS. 17, 18, 19 and 20 the button 18 for regulating intensity is no longer at the level of the articulation axis of the handle 3, but rather is at the end 17 of the sleeve 2 facing the end of the handle 3. By displacing the button 18 in a longitudinal slot 19 (FIGS. 17 and 19) or in an extension 20 (FIGS. 18, 20), locking in the chosen position is possible, as well as regulation of the course of the handle 3.

As in FIGS. 15 and 16, the regulating button 18 comprises a pin 24 which limits the path of the end of the handle 3.

The handle comprises a notch 21 for passage of the button 18 which makes use of the abutment or pin 24. When the button 18 is displaced outside of the notch 21, the end 16 of the handle 3 may not be completely pushed in, and the path is thus limited. When the button 18 is facing the notch 21, the handle 13 may be pushed all the way in, and the path is thus maximum.

FIG. 21 is a sectional view of the head of the apparatus. It shows the spark-discharging electrode 6 of which the distance from the skin may be adjusted by a button 25 along the arrows F1, F2. The button 25 may be fixed to the electrode 6 or be provided with gear reduction means permitting a micrometric displacement.

Moreover, there could also be a fixed spark-discharging electrode 6 and only the plane serving as the electrode 5 for contact with the skin could be displaced.

In FIG. 22, the spark-discharging electrode 6 may be displaced relative to the skin and to the other electrode 5 by means of a threaded ring 27 and a threaded rod 28 disposed on the principal body of the said spark-discharging electrode 6.

In FIG. 23, the contact electrode 5 may be removable and, depending on its thickness 29 permit automatically and adjustably spacing the spark-discharging electrode 6.

In FIG. 24, the adjustment of the intensity may be made by clamping more or less strongly the quartz crystals 31, in the metallic support 32 with the compression screw 30; this adjustment may be fixed or effected on demand, and in a variable manner by a knob 33 integral with or separable from the screw 30, permitting adjustment of the intensity from the exterior of the apparatus and compensating for the wearing away of the crystals. If desired, this arrangement permits standard exchange of the crystals.

I claim:

1. Apparatus for providing relief from pain and contractions via the discharge of sparks of piezo-electric origin resulting from direct application of the apparatus to the skin of a patient, comprising (a) a handle;

(b) means connected with said handle for generating a piezo-electric charge including actuating means arranged within said handle and a pair of poles; and (c) bipolar electrode means connected with said poles of said piezo-electric generator means, said bipolar electrode means including (1) at least one metallic electrode connected with said handle and arranged for direct contact with the skin of the patient, said contact electrode being connected with one pole of said generator means; and (2) at least one discharge electrode connected with said handle and recessed from said contact electrode, said discharge electrode being connected with the other pole of said generator means, said spaced arrangement of said contact and discharge electrodes producing a series of sparks from said discharge electrode to said contact electrode which are thereby applied to the skin of the patient.

2. Apparatus as defined in claim 1, wherein said contact electrode comprises a generally rectangular head portion of the apparatus arranged at one end of said handle, said discharge electrode being arranged in the transverse median portion of said head portion.

3. Apparatus as defined in claim 1, wherein the height of said at least one discharge electrode is less than the height of said contact electrode.

4. Apparatus according to claim 1, wherein said at least one metallic electrode for direct contact with the skin comprises points directed toward points of said at least one discharge electrode, which points favor discharge between the bipolar electrode means at the time of their operation out of direct contact with the skin.

5. Apparatus according to claim 1, wherein said apparatus comprises a distal end forming a generally rectangular head portion, said at least one metallic electrode being centrally disposed in said head portion in the form of a contact strip, said at least one discharge electrode comprising a row of discharge points on either side of said contact strip.

6. Apparatus according to claim 1, wherein said at least one metallic electrode comprises a contact plate having at least one cavity formed therein, said at least one discharge electrode comprising at least one discharge point each said discharge point being received in a corresponding said at least one cavity, each said at least one discharge point being recessed relative to said contact plate.

7. Apparatus according to claim 1, wherein said at least one metallic electrode and said at least one discharge electrode are formed by a row of parallel disks of alternating polarity, the disks of said discharge electrode having a lesser diameter than the disks of said metallic electrode, thereby to be recessed therefrom.

8. Apparatus according to claim 1, further comprising means for regulating the intensity of said series of sparks.

9. Apparatus according to claim 1, further comprising means for automatically and adjustably varying the extent to which said at least one discharge electrode is recessed from said at least one metallic electrode.

10. Apparatus according to claim 1, wherein said at least one discharge electrode is fixed relative to said handle, and said at least one metallic electrode is movable relative to said at least one discharge electrode.

11. Apparatus according to claim 1, wherein said at least one metallic electrode is fixed relative to said handle, and said at least one discharge electrode is movable relative to said at least one metallic electrode.

12. Apparatus according to claim 1, wherein said at least one metallic electrode is removable, thereby to permit manual adjustment of the extent to which said at least one discharge electrode is recessed from said at least one metallic electrode, by substitution of a said at least one metallic electrode of a different thickness.

* * * * *